United States Patent
Katsumi

(12) 
(10) Patent No.: US 6,274,565 B1
(45) Date of Patent: Aug. 14, 2001

(54) INHIBITOR OF ACTIVATION OF β-GLUCAN RECOGNITION PROTEIN

(75) Inventor: Yoichi Katsumi, Hyougo (JP)

(73) Assignee: Wako Pure Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/211,043

(22) Filed: Dec. 15, 1998

(30) Foreign Application Priority Data

Dec. 16, 1997 (JP) .................................... 9-363960

(51) Int. Cl.$^7$ .................. A01N 43/04; A61K 31/715; A61K 35/64
(52) U.S. Cl. .................. 514/54; 424/538; 424/193.1; 536/55.1; 536/123.1; 536/123.12; 536/124; 435/4; 435/18; 435/19; 435/23; 435/25; 435/201; 435/206; 435/207; 435/208
(58) Field of Search .............................. 435/4, 201, 205, 435/206, 207, 208; 514/54; 536/55.1, 123.1, 124, 123.12; 424/193.1, 538

(56) References Cited

U.S. PATENT DOCUMENTS 4,970,152 * 11/1990 Ashida et al. .................. 435/19

FOREIGN PATENT DOCUMENTS

| 0 270 039 | 6/1988 | (EP) . |
| 0 330 991 | 9/1989 | (EP) . |
| 0 333 187 | 9/1989 | (EP) . |
| 0 397 880 | 11/1990 | (EP) . |
| WO 83/02123 | 6/1983 | (WO) . |

OTHER PUBLICATIONS

Yoshida et al., Biochemical and Biophysical Research Communication, vol. 141, No. 3, pp. 1177–1184, Dec. 30, 1986. (Discussed in the Specification).

Ashida, Insect Biochem. vol. 11, pp. 57–61, 63–65, 1981. (Discussed in the Specification).

Ochiai et al., The Journal of Biological Chemistry, vol. 263, No. 24, pp. 12056–12062, 1988. (Discussed in the Specification).

Tsuchiya, FEMS Immunology and Medical Microbiology, 15, pp. 129–134, 1996. (Discussed in the Specification).

First Department of Biochemistry, School of Medicine, Showa University; XP–002063489, Chapter 25; *Diverse Biological Activity of PSK (Krestin) , A Protein–Bound Polysaccharide From Coriolus Versicolor (FR.) Quel.*; Hiroshi Sakegami et al.

Institute of Biochemistry and Biotechnology, Technical University of Braunschweig; Carbohydrate Polymers 24 (1994) 193–197; *Acetylation of a β–1, 6–branched β–1, 3–glucan, yielding Schizophyllan–acetate*; Andre Albrecht, Udo Rau.

* cited by examiner

Primary Examiner—James O. Wilson
(74) Attorney, Agent, or Firm—Armstrong, Westerman, Hattori, McLeland & Naughton LLP

(57) ABSTRACT

The present invention relates to an inhibitor of an activation of β-glucan recognition protein in a body fluid of an insect comprising a sugar compound comprising plural member of sugar residues, at least one of which have a substituent at the 6-position, the sugar residues being bonded mainly through β 1→3 linkage with one another, a process for inhibiting the activation; an agent for treating the body fluid of an insect, a process for the treatment; a novel agent for measuring peptidoglycan simply and effectively, and a process for the measurement.

The present invention is markedly effective in that a reagent, which are obtained form a body fluid of an insect, can easily be obtained.

13 Claims, 2 Drawing Sheets

INHIBITOR OF ACTIVATION OF β-GLUCAN RECOGNITION PROTEIN

BACKGROUND OF THE INVENTION

The present invention relates to an inhibitor of an activation of β-glucan recognition protein in a body fluid of an insect, a process for inhibiting the activation; an agent for treating a body fluid of an insect, a process for the treatment; a novel agent for measuring peptidoglycan, and a process for the measurement.

Peptidoglycans (hereinafter abbreviated as PG) are glycoprotein containing N-acetylmuramic acid residue or N-glycolylmuramic acid residue and D-amino acid residues, and they play, as bacterial cell wall components, an important role for retention of the form of bacteria.

PG have various biological activities such as various functions to immune response cells (e.g. macrophages, B lymphocytes, T lymphocytes, etc.), destruction of blood platelets, growth enhancement of fibroblasts, enhancement of bone resorption, activation of complements, enhancement or inhibition of humoral immune responses, enhancement of cellular immunity, stimulation of cell endotherial systems, transient leukopenia and subsequent hypercytosis, enhancement of the functions of interferon inducing factors, potentation of natural resistance, induction of experimental autoimmune diseases, pyrogen functions, enhancement of sensitivity to the toxicity of endotoxins (hereinafter abbreviated as ET), enhancement or inhibition of sleep, formation of epithelioid granulomas, functions of hemorrhagic necrosis at sites treated with tubercle bacillus or the like and acute or chronic toxicity.

While ET are contained only in Gram-negative bacteria, PG are contained both in Gram-positive bacteria and Gram-negative bacteria. And PG are contained in the cell walls to form thick layers at the outermost shells of cell walls in the Gram-positive bacteria, and are contained in the cell walls to form thin layers inside outer membranes of the cell walls in the Gram-negative bacteria. Almost all procaryotes contain PG in their cell walls except for archaebacteria (e.g. methane bacteria, highly acidophilic bacteria, etc.) which contain neither ET nor PG. On the other hand, PG are not contained in the cell components of eukaryotes such as mammals and hence it is considered that bacteria are present where PG is present.

Therefore, PG measurement is useful for detecting a trace amount of microorganisms such as bacteria and blue-green algae (Cyanophyceae), which contain PG as a constituent of cell wall, and is expected to be applicable to, for example, safety tests of drugs and the like, microbial tests of water and foods, and diagnoses of infectious diseases.

As a process for measuring PG, there has been reported, for example, a method using a reagent derived from a body fluid of an insect (JP-B 7-114707). The body fluid of an insect contains factors constituting the pro-phenol oxidase (hereinafter abbreviated as proPO) cascade, and usually, they are not yet activated (inactive type factors). The body fluid of an insect contains, as one of the factors, a substance which binds to PG to activate the proPO cascade (PG recognition protein). The process for measuring PG mentioned above is characterized in utilizing such property of PG contained in the sample as binding to this PG recognition protein in a body fluid of an insect to activate the proPO cascade. However, the body fluid of an insect also contains substance which binds to β-1,3-glucan (hereinafter abbreviated as β G) to activate the proPO cascade ( β G recognition protein, which is hereinafter abbreviated as β GRP) [Yoshida, H., Ochiai, M., and Ashida, M. (1986) Biochem. Biophys. Res. Commun. 141, 1177–1184]. So, in the process mentioned above, it is necessary to remove β GRP from the body fluid of an insect before making it into the reagent to measure the PG specifically by affinity chromatography or the like, and this removing process is complicated and troublesome.

SUMMARY OF THE INVENTION

The present invention has been made in view of such prior state of the art as above and the object thereof is to provide a novel inhibitor of an activation of β GRP in the body fluid of an insect, a process for inhibiting the activation by the use of said inhibitor, an agent for treating a body fluid of an insect, a treating process using said agent, an effective reagent for measuring PG, and a process for measuring PG, more particularly.

The present invention provides an inhibitor of the activation of β GRP in a body fluid of an insect comprising a sugar compound comprising plural member of sugar residues, at least one of which have a substituent at the 6-position, the sugar residues being bonded mainly through β 1→3 linkage with one another.

The present invention also provides a process for inhibiting the activation of β GRP comprising treating a body fluid of an insect with a sugar compound comprising plural member of sugar residues, at least one of which have a substituent at the 6-position, the sugar residues being bonded mainly through β 1→3 linkage with one another.

The present invention further provides an agent for treating a body fluid of an insect comprising a sugar compound comprising plural member of sugar residues, at least one of which have a substituent at the 6-position, the sugar residues being bonded mainly through β 1→3 linkage with one another.

The present invention still further provides a process for treating a body fluid of an insect comprising contacting a body fluid of an insect with a sugar compound comprising plural member of sugar residues, at least one of which have a substituent at the 6-position, the sugar residues being bonded mainly through β 1→3 linkage with one another.

The present invention additionally provides a reagent for measuring PG comprising a body fluid of an insect and a sugar compound comprising plural member of sugar residues, at least one of which have as a substituent at the 6-position, the sugar residues being bonded mainly through β 1→3 linkage with one another.

The present invention still additionally provides a process for measuring PG comprising reacting a sample with a body fluid of an insect, in the presence of a sugar compound comprising plural member of sugar residues, at least one of which have a substituent at the 6-position, the sugar residues being bonded mainly through β 1→3 linkage with one another.

BRIEF DESCRIPTION OF THE DRAWINGS

In FIG. 1, —□— shows the results obtained by using curdlan, —◇—the results obtained by using schizophyllan, —○— the results obtained by using CMEC, and —△— the results obtained by using laminaran.

In FIG. 2, —□— shows the results obtained by using laminarin, —◇— the results obtained by using pachyman, —○— the results obtained by using Krestin™, and —△— the results obtained by using zymosan A.

DETAILED DESCRIPTION OF THE PREFERED EMBODIMENTS

Figure 1:
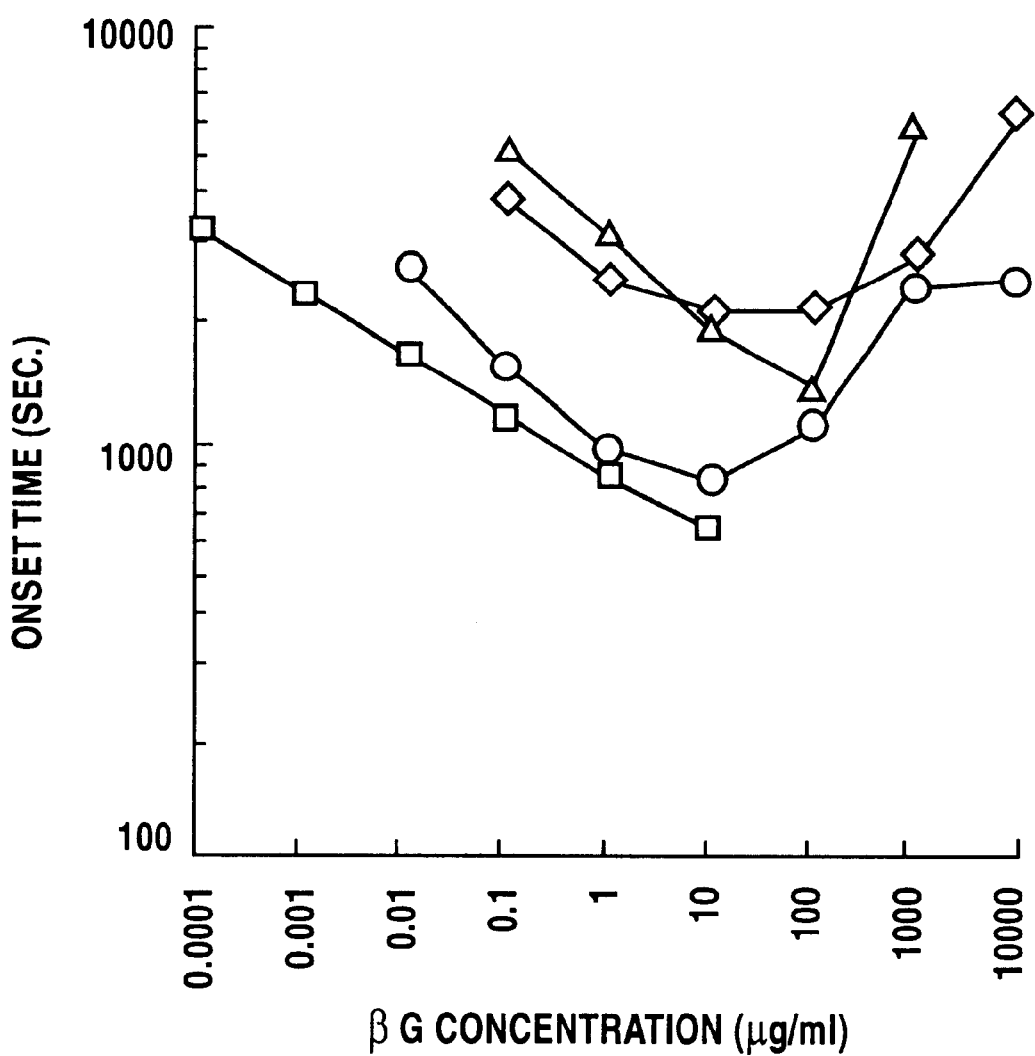
FIG. 1 shows the results of plotting onset time corresponding to individual β G concentrations on log-log graph paper in the case of using curdlan, schizophyllan, carboxymethylated curdlan (CMEC) or laminaran as β G which were obtained in Experiment Example 1.

Under the circumstances as above, in order to find a substance capable of inhibiting the activation of β GRP in a body fluid of an insect, the present inventors have earnestly investigated and consequently found that a sugar compound comprising plural member of sugar residues, at least one of which have a substituent at the 6-position, the sugar residues being bonded mainly through β 1→3 linkage with one another, has the inhibitory effect. In addition, the present inventors have found that the use of said compound as an inhibitor of the activation of β GRP in a body fluid of an insect can inhibit the activation of said β GRP and makes it possible to obtain a reagent for measuring PG easily and specifically.

The sugar compound comprising plural member of sugar residues, at least one of which have a substituent at the 6-position, the sugar residues being bonded mainly through β 1→3 linkage with one another, which is used in the present invention (hereinafter abbreviated as "the present sugar compound") is not particularly limited so long as it has at least one sugar residue having a substituent at the 6-position and can inhibit the activation of β GRP.

Sugar residues constituting the present sugar compound include, for example, tetrose residues such as threose residue, erythrose residue and erythrulose residue; pentose residues such as ribose residue, deoxyribose residue, arabinose residue, xylose residue, lyxose residue, ribulose residue, xylulose residue, arabinulose residue and lyxulose residue; hexose residues such as glucose residue, mannose residue, allose residue, altrose residue, galactose residue, talose residue, idose residue, gulose residue, fucose residue, fructose residue, sorbose residue, tagatose residue and psicose residue; amino sugar residues such as glucosamine residue, galactosamine residue and acetylglucosamine residue; sialic acid residues such as acetylneuraminic acid residue; and sugar alcohol residues such as sorbitol residue, inositol residue, mannitol residue, ribitol residue, erythritol residue, arabitol residue and xylitol residue. Of these, the hexose residues are preferable and glucose residue is particularly preferable.

The number of β 1→3 linkages in the present sugar compound is properly selected in the range of two or more, preferably 2 to 1,000, more preferably 10 to 600, still more preferably 20 to 600. As the β 1→3 linkage, a β 1→3 hexoside linkage is preferable, among which glucoside linkage is more preferable.

The present sugar compound may be either linear or branched.

In the present sugar compound, all or some parts of the sugar residues have substituents at the 6-position, and preferable ones are those containing the substitutents at the 6-position, for example, of hexose residues such as glucose residue, mannose residue, allose residue, altrose residue, galactose residue, talose residue, idose residue, gulose residue, fucose residue, fructose residue, sorbose residue, tagatose residue and psicose residue. Of these, glucose residue is preferable.

The substituent at the 6-position is not particularly limited so long as it does not remarkably lower the water-solubility of the present sugar compound, including, for example, hydrophilic groups and groups which do not deteriorate the hydrophilicity.

The hydrophilic groups include, for example, carboxy lower alkyl groups such as carboxymethyl and carboxyethyl; hydroxy lower alkyl groups such as hydroxyethyl and hydroxypropyl; sulfo lower alkyl groups such as sulfopropyl; and sulfonic group. The groups which do not deteriorate the hydrophilicity include, for example, lower alkyl groups such as methyl, ethyl and n-propyl ; lower acyl groups derived from carboxylic acids such as acetyl and propionoyl; sugar residues such as glucose residue, mannose residue and galactose residue; and sugar chains composed of two or more of these sugar residues.

The number of substituents in the present sugar compound is not particularly limited so long as the present sugar compound can inhibit the activation of β GRP and its solubility is not remarkably lowered, and preferable examples of the present sugar compound are those in which 10% or more of the groups of the sugar compound capable of being substituted are substituted by the groups as mentioned above.

As the present sugar compound, polysaccharides are preferable. Specific examples of the polysaccharides are those naturally obtainable such as schizophyllan, laminarin, laminaran, Krestin™, pachyman and zymosan A, which are obtained from cell walls of various bacteria (e.g. the genus Alcaligenes, the genus Agrobacterium, the genus Rhizobium, etc.), yeasts (e.g. the genus Saccharomyces, etc.), mushrooms (e.g. *Cortinellus shiitake, Schizophyrum commune, Coriolus versicolor*), etc., and algae (e.g. the genus Eisenia, the genus Laminaria, etc.).

The present sugar compound also includes those obtained by introducing the above-exemplified substituent(s) into sugars having as a constituent no sugar residue having a substituent at the 6-position, according to a conventional method described, for example, in Munio Kotake "Daiyukikagaku Vol. 19 ", 7th ed., pp. 70–101, ASAKURA SHOTEN Ltd., published on May 10, 1967, A. E. Clarke et al., Phytochemistry. 1. 175–188 (1967), and T. Sasaki et al., Europ. J. Cancer, 15, 211–215 (1979).

The sugars having as a constituent no sugar residue having a substituent at the 6-position include polysaccharides such as curdlan, sclerotan, lentinan, coriolan, lichenin, paramylon and callose. As these polysaccharides, there can be exemplified those obtained from cell walls of various bacteria (e.g. the genus Alcaligenes, the genus Agrobacterium, the genus Rhizobium, etc.), yeasts (e.g. the genus Saccharomyces, etc.), mushrooms (e.g. *Cortinellus shiitake, Schizophyrum commune, Coriolus versicolor*), etc., and algae (e.g. the genus Eisenia, the genus Laminaria, etc.).

A typical example of the present sugar compound obtained by introducing the substituent as mentioned above is carboxymethylated curdlan.

The present sugar compound still further includes polysaccharides obtained by additionally introducing the above-exemplified substituent(s) into naturally obtainable polysaccharides comprising plural member of sugar residues, at least one of which have the above-exemplified substituent at the 6-position according to a conventional method.

As a method for introducing a substituent into the 6-position of at least one of the sugar residues, there can be exemplified the conventional introduction methods mentioned above.

Of the above-exemplified present sugar compounds, preferable are sugar compounds having one or more units composed of one sugar residue having a substituent at the 6-position and two sugar residues having no substituent at the 6-position, the sugar residues being through β 1→3 linkages with one another. Specific examples of such sugar compounds are schizophyllan, carboxymethylated curdlan, laminarin, laminaran, Krestin™, etc.

Of these, particularly preferable are sugar compounds having only a glucose residue as the sugar residues and the substituent at the 6-position is a glucose residues. Preferable specific examples thereof are schizophyllan, Krestin™.

The concentration of the present sugar compound to be contained in a body fluid of an insect is properly chosen in the range of usually 1 μg to 1 g, preferably 5 μg to 100 mg, more preferably 10 μg to 10 mg relative to 100 μg of β GRP in the body fluid, which can be measured by a conventional manner, for instance, one disclosed in Ochiai, M., Ashida M. (1988) J. Biol. Chem. 263, 12056–12062. More practically, however, the concentration of the present sugar compound to be used is properly chosen in the range of usually 1 μg to 1 g, preferably 5 μg to 100 mg, more preferably 10 μg to 10 mg relative to 1 ml of the body fluid.

The present sugar compound may be used either a single compound or a proper combination thereof.

By treating the body fluid of an insect with the present sugar compound, the activation of β GRP in the body can be inhibited.

The body fluid of an insect is designated hemolymph. There is no limitation to the insects which can give body fluids, but larger ones with known rearing methods thereof are preferable. Examples such insects are *Manduca sexta*, *Galleria melonella*, *Hyalophora cecropia* and *Bombyx mori* belonging to the order Lepidoptera; *Sarcophaga peregrina* and *Musca* belonging to the order Diptera; *Locusta* and *Migratoria Teleogryllus* belonging to the order Orthoptera; and *Cerambyx* belongiong to the order Coleoptera. The insect is not limited to them. Bombyx such as *Bombyx mori Linne*, *Bombyx mori manarina Moore*, *Oberthüria Falcigera Butler*, *Andraca gracilis Butler* are preferable for easily obtained. The body fluid obtained from both an imago or a larva can be used. A larva is preferable for reasonable to harvest.

As a method for collecting the body fluid from the above-exemplified insect, there can be exemplified a method of placing the insect on ice to stop its moving, physiological saline containing sucrose including a cane sugar factor (polymeric substances included in a sugar cane and comprising glucose, amino acids, etc.) as an impurity, or containing a cane sugar factor itself, or physiological saline containing a serine protease inhibitor such as (p-amidinophenyl) methanesulfonyl fluoride (p-APMSF), phenylmethanesulfonyl fluoride (PMSF), diisopropylfluorophosphoric acid (DFP), p-nitrophenyl p-guanidinobenzoate (NPGB), dihydroxychloromethylcoumarin (DCC) or the like is injected into body cavity of the insects, allowing the insect to stand for a while, and then collecting body fluid from the body cavity; and a method of adding body fluid to a solution isotonic to an insect body fluid to be collected which contains the above-exemplified serine protease inhibitor (Ashida, M., Insect Biochem., 11, 57–65, 1981, JP-A 1-142466). The body fluid of an insect thus obtained is centrifuged to be freed of hemocytes, and then dialyzed, whereby there is obtained plasma which can be used for purpose of the present invention.

In place of or in combination of the body fluid naturally obtained, a product having the necessary effect for the present invention, which is obtained by genetic engineering technology, can also be used.

The body fluid thus prepared can be used as it is for the purpose of the present invention, and further it may be made into a solution containing the body fluid in a solvent such as a buffer solution, water, etc. Still further, the body fluid may be processed such as purification, fractionation, etc.

As such body fluid, use can be made of commercially available ones [e.g. an SLP (trade name ,Wako Pure Chemical Industries, Ltd.) reagent set, manufactured and sold by Wako Pure Chemical Industries, Ltd.].

In the present invention, a method for treating the body fluid with the present sugar compound is not particularly limited so long as it enables the present sugar compound to be finally present in the body fluid. As the most usual method, there can be exemplified a method of dissolving the present sugar compound in the body fluid to make them present together, a method of mixing the body fluid with a solution containing the present sugar compound, etc.

The solvent for preparing the solution containing the present sugar compound is not particularly limited so long as it does not activate the proPO cascade and does not lessen the inhibitory effect of the present sugar compound on the activation of β GRP. The solvent includes, for example, distilled water, buffer solutions, etc. As the buffers which constitute the buffer solutions, all buffers usually used in the art can be used. Specific examples of the buffer are phosphates, borates, acetates, Tris buffers, Good's buffers, etc. The concentration of the buffer used may be properly chosen in a concentration range usually employed in the art.

The body fluid thus obtained is usually used after being incorporated with, for example, a substance (including so-called synthetic substrates) which is a substrate for an enzyme activated by the reaction of the body fluid with β G and/or PG and produces a suitable coloring matter or the like (including fluorescent or luminescent ones) owing to the action of the enzyme.

The reagent which can specifically measure only PG (hereinafter abbreviated as the PG reagent) can easily be obtained by incorporating the present sugar compound into the body fluid in such a concentration as mentioned above.

The process for measuring PG of the present invention may be practiced according to a conventional measuring process using the body fluid of an insect containing the present sugar compound described above in the above concentration range. Other reagents used may be properly chosen according to the conventional measuring process.

That is, PG in a sample can be specifically measured by subjecting the sample to the measurement in the presence of the present sugar compound according to the conventional measuring process using the body fluid of an insect.

In the process for measuring PG of the present invention, it is sufficient that in reacting the body fluid of an insect with a sample, the present sugar compound is finally made present in the above concentration range. A method for this presence is not particularly limited.

Specific examples of the method are a method of incorporating the present sugar compound into the body fluid of an insect and then mixing the resulting solution with a sample, and a method of diluting a sample with the above-exemplified solution such as buffer solution, containing the present sugar compound and mixing the diluted sample with the body fluid of an insect.

Preferable examples of the conventional measuring process using the PG reagent are a process of mixing and reacting a sample with the PG reagent, measuring the enzyme activity such as an esterase hydrolyzing N-α-benzoyl-L-arginine ethyl ester (BAEEase), prophenoloxidase activating enzyme (PPAE) or phenoloxidase (PO) in the reaction solution after a definite time according to a conventional method, and calculating the amount of PG from a calibration curve previously obtained by use of standard solutions containing known concentrations of PG by the same procedure as above (M. Tsuchiya et al. FEMS Immunology and Medical Microbiology 15 (1996) 129–134, JP-A 7-184690, etc.), and a process of mixing a sample with the PG reagent and then measuring a time required for the amount of the reaction product due to PO activity to reach a definite value, which utilizes the phenomenon that a time required for proPO to be activated into PO is dependent on the PG concentration in the sample (M. Tsuchiya et al. FEMS Immunology and Medical Microbiology 15 (1996) 129–134, etc.).

Other ingredients used in these conventional measuring processes include, for example, substrates for the enzyme to be measured such as 3,4-dihydroxyphenylalanine (DOPA) and synthetic substrates, coupling enzymes, coenzymes, and optionally color developing agents, activators, stabilizers, surfactants, etc., which are used in conventional processes for measuring an objective enzyme activity.

Although varied depending on the kind of an enzyme to be measured, etc., the reaction pH in the measuring process of the present invention is usually pH 4 to 11, preferably pH 6 to 9. A buffer may be used for maintaining the reaction pH. The buffer is not particularly limited in the kind and using concentration so long as it has no undesirable influence on the reaction. The buffer includes, for example, phosphates, borates, acetates, Tris buffers, Good's buffers, etc.

The reaction temperature and the reaction time are not particularly limited so long as they are a temperature at which the reaction proceeds and a time for which the reaction proceeds. The reaction temperature is usually 0 to 50° C., preferably 4 to 30° C. The reaction time is properly chosen in the range of usually 1 second to 20 hours, preferably 10 seconds to 2 hours.

In the measurement, it is preferable that divalent metal ions such as $Ca^{2+}$ and $Mg^{2+}$ are present in a concentration range of 0.001 to 1,000 mM, preferably 5 to 100 mM.

A sample which can be subjected to measurement by the process for measuring PG of the present invention is not particularly limited so long as the detection of the presence of microorganisms in the sample is necessary. The sample includes, for example, washing water for semiconductors, body fluids (e.g. blood, plasma, serum and cerebrospinal fluid), urine, tap water, factory wastes, foods, drinks, washings after washing medical instruments, etc.

For instance, the measuring process of the present invention may performed as follows.

That is, the above-exemplified sample is mixed with the body fluid of an insect containing the present sugar compound, and the reaction is carried out under definite reaction conditions (for example, at 0 to 50° C., preferably 4 to 30° C., for 1 second to 20 hours, preferably 10 seconds to 2 hours) . A reaction time required for the absorbance of the reaction solution to reach a predetermined threshold value is measured by means of, for example, a commercially available Microplate Reader Thermo-Max (mfd. by Molecular Devices Co.), Toxinometer (mfd. by Wako Pure Chemical Industries, Ltd.) or the like. The PG content of the sample can be calculated from a calibration curve showing the relationship between PG concentration and reaction time which has previously been obtained by use of standard solutions containing known concentrations of PG by the same procedure as above.

The PG reagent for measuring PG of the present invention is used for measuring PG in various samples in which the detection of the presence of microorganisms is necessary, such as washing water for semiconductors, body fluids such as blood, plasma, serum and cerebrospinal fluid, urine, tap water, factory wastes, foods, drinks and washings after washing medical instruments. Said reagent is prepared so as to contain the same reagents as those used in the above-exemplified measuring process using the body fluid containing the present sugar compound as an inhibitor of the activation of β GRP. Preferable properties, using concentrations, etc. of the constituents of said reagent are as described above.

The present invention is illustrated below in further detail with reference to Reference Examples, Examples and Comparative Examples, which should not be construed as limiting the scope of the invention.

In the following Reference Examples and Examples, distilled water and water for injection (manufactured and sold by Otsuka Pharmaceutical Co. Ltd.) were used after confirmation that β G and/or PG were not detected in the distilled water and the water for injection by using a commercially available SLP (trade name, Wako Pure Chemical Industries, Ltd) reagent set (available from Wako Pure Chemical Industries, Ltd.).

EXAMPLE

Experiment Example 1

Study of the reactivity of the body fluid with various β 1,3-glucans

[Reagents]

(1) Reagent

A fraction obtained from the body fluid of silkworms (Kinsyushowa *Bombyx mori*) by fractionation according to the method described in Ashida, M., (1981) Insect Biochem., 11, 57–65 was used as a reagent (β GRP concentration: 1 μg/ml or less).

The β GRP concentration in the body fluid was measured according to the method described in Ochiai, M., Ashida, M. (1988), J. Biol. Chem. 263, 12056–12062.

(2) DOPA • calcium solution

DOPA and calcium chloride were dissolved in 0.1 M MOPS buffer (pH 6.5) to concentrations of 6 mM and 24 mM, respectively, and the solution was filtered through a Zetapor membrane (mfd. by Cuno). The filtrate was used as a DOPA • calcium solution.

(3) β-1,3-Glucan solutions;

β-1,3-Glucan solutions were prepared as follows.

Curdlan (available from Wako Pure Chemical Industries, Ltd.): Curdlan was dissolved in 0.25 N NaOH to a concentration of 1 mg/ml and the solution was diluted with distilled water to prepare serial dilutions in a concentration range of 10 pg/ml to 10 μg/ml.

Schizophyllan (available from KAKEN SEIYAKU CO, LTD.): Serial dilutions in a concentration range of 10 ng/ml to 10 mg/ml were prepared by diluting a 10 mg/ml schizophyllan solution with distilled water.

Carboxymethylated curdlan (CMEC, available from Wako Pure Chemical Industries, LTD.): Carboxymethylated curdlan was dissolved in distilled water to a concentration of 10 mg/ml and the solution was diluted with distilled water to prepare serial dilutions in a concentration range of 10 ng/ml to 10 mg/ml.

Laminaran (available from Tokyo Kasei Kogyo Co, Ltd.): Laminaran was dissolved in distilled water to a concentration of 10 mg/ml and the solution was diluted with distilled water to prepare serial dilutions in a concentration range of 10 ng/ml to 10 mg/ml.

Laminarin (available from Sigma Chemical Co. Ltd.): Laminarin was dissolved in distilled water to a concentration of 10 mg/ml and the solution was diluted with distilled water to prepare serial dilutions in a concentration range of 10 ng/ml to 10 mg/ml.

Pachyman (available from Calbiochem-Nobabiochem Co.): Pachyman was dispersed in distilled water to a concentration of 1 mg/ml and the dispersion was diluted with distilled water to prepare serial dilutions in a concentration range of 1 ng/ml to 1 mg/ml.

Krestin™ (available from Kureha Chemical Industry Co., Ltd.): Krestin™ was dissolved in distilled water to a concentration of 10 mg/ml and the solution was diluted with distilled water to prepare serial dilutions in a concentration range of 10 ng/ml to 10 mg/ml.

Zymosan A (available from Sigma Chemical Co. Ltd.): Zymosan A was dispersed in distilled water to a concentration of 1 mg/ml and the dispersion was diluted with distilled water to prepare serial dilutions in a concentration range of 1 ng/ml to 1 mg/ml.

[Measuring instrument]

Measurement was carried out by means of a Microplate Reader Thermo-Max (mfd. by Molecular Devices Co.) under the following conditions:

Temperature: 30° C.

Time: 1 hour and 40 minutes

Onset OD: 0.01

Measuring wavelength: 650 nm.

The data were analyzed by means of Soft Max version 2.32.

[Procedure]

With 750 µl of the aforesaid reagent was mixed 375 µl of the aforesaid DOPA • calcium solution to obtain an enzyme • substrate solution. Into a 96-well microtiter plate made of polystyrene were dispensed 50 µl of the enzyme • substrate solution and 50 µl of each of the various β-1,3-glucan solutions having the predetermined concentrations, and measurement was carried out with the Microplate Reader under the conditions described above.

[Results]

Figure 2:
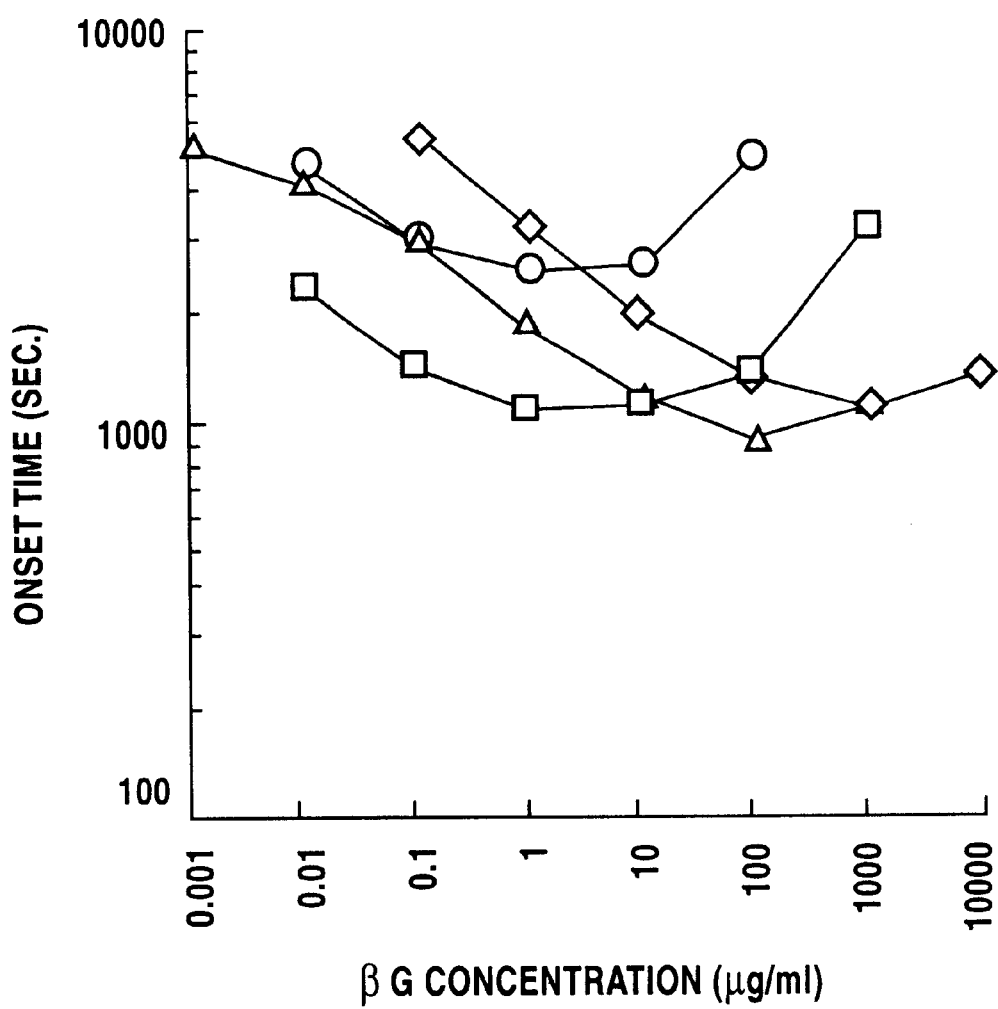
FIG. 2 shows the results of plotting onset time corresponding to individual β G concentrations on log-log graph paper in the case of using laminarin, pachyman, Krestin™ (trade name, Kureha Chemical Industry Co., Ltd. a glycoprotein derived from Coriolus versicoler) or zymosan A as β G, which were obtained in Experiment Example 1.

FIG. 1 shows the results of plotting onset time corresponding to individual β-1,3-glucan concentrations on log-log graph paper in the case of using curdlan, schizophyllan, CMPS or laminaran as β-1,3- glucan. FIG. 2 shows the results of plotting onset time corresponding to individual β-1,3-glucan concentrations on log-log graph paper in the case of using laminarin, pachyman, Krestin™ or zymosan A as β-1,3-glucan. In FIG. 1 and FIG. 2, the axis of abscissa refers to the concentration of each β-1,3-glucan and the axis of ordinate to onset time.

In FIG. 1, —□— shows the results obtained by using curdlan, —◇— the results obtained by using schizophyllan, —○— the results obtained by using CMPS, and —△— the results obtained by using laminaran.

In FIG. 2, —□—shows the results obtained by using laminarin, —◇— the results obtained by using pachyman, —○— the results obtained by using Krestin™, and —△— the results obtained by using zymosan A.

As is clear from the results shown in FIG. 1 and FIG. 2, when curdlan having no sugar residue having a substituent at the 6-position is reacted with the reagent, the onset time is decreased in proportion to an increase of the curdlan concentration. On the other hand, when each sugar compound having at least one sugar residue having a substituent at the 6-position is reacted with the reagent, the onset time is increased in the following concentration range of the sugar compound: schizophyllan 10 µg/ml or more (concentration in the reaction solution: 5 µg/ml or more), CMPS 100 µg/ml or more (concentration in the reaction solution: 50 µg/ml or more), laminaran 1 mg/ml or more (concentration in the reaction solution: 500 µg/ml or more), laminarin 10 µg/ml or more (concentration in the reaction solution: 5 µg/ml or more), pachyman 10 mg/ml or more (concentration in the reaction solution: 5 mg/ml or more), Krestin™ 10 µg/ml or more (concentration in the reaction solution: 5 µg/ml or more), zymosan A 1 mg/ml or more (concentration in the reaction solution: 500 µg/ml or more). This fact suggests that the sugar compounds comprising plural member of sugar residues, at least one of which have a substituent at the 6-position, the sugar residues being bonded mainly through β 1→3 linkage with one another, reduce the reactivity of the reagent with β G, namely, they can inhibit the activation of β GRP in the reagent.

EXAMPLE 1

Study of the reactivity of the body fluid containing the present invention's sugar compound with β G and PG

[Reagents]

(1) the reagent; The same as in Experiment Example 1.

(2) DOPA • calcium solution; The same as in Experiment Example 1.

(3) β-1,3-Glucan solutions;

β-1,3-Glucan solutions were prepared as follows by using schizophyllan and Krestin™ which had been found to have inhibitory effect on β GRP activation in Experiment Example 1.

Schizophyllan (available from KAKEN SEIYAKU CO,LTD. ): A 10 mg/ml of schizophyllan ampoule was used as a schizophyllan solution.

Krestin™ (available from Kureha Chemical Industry Co., Ltd.): Krestin™ was dissolved in distilled water to a concentration of 5 mg/ml and the resulting solution was used as a Krestin™ solution.

(4) PG standard solutions;

According to the method of Schleifer et al. (Schleifer, K. H., and Kandlar, O., Bacteriol. Rev., 36, 407–477 (1972)), 1 g of dried cells of *Micrococcus luteus* were treated to obtain 95 mg of trypsinized cell walls (PG). 20 Milligrams of the trypsinized cell walls (PG) were added to 20 ml of water for injection (mfd. by Otsuka Pharmaceutical Co., Ltd.) and dispersed therein by ultrasonication to obtain a PG stock solution. When used, the PG stock solution was diluted with distilled water to prepare serial dilutions in a concentration range of 1 ng/ml to 1 µg/ml as PG standard solutions.

(5) β G standard solutions;

A solution of 10 mg of curdlan (available from Wako Pure Chemical Industries, Ltd.) in 10 ml of a 0.25 N sodium hydroxide solution was used as a β G stock solution. When used, the β G stock solution was diluted with distilled water to prepare serial dilutions in a concentration range of 10 pg/ml to 10 µg/ml as β G standard solutions.

[Measuring instrument]

The same as in Experiment Example 1.

[Procedure]

Into a glass test tube previously subjected to dry heat sterilization at 250° C. for 2 hours were poured 575 µl of the reagent, 375 µl of the DOPA • calcium solution and 175 µl of each β-1,3-glucan solution, and mixed to obtain a liquid reaction reagent. Subsequently, 50 μl of each β G standard solution having the predetermined concentration or each PG standard solution having the predetermined concentration and then 50 μl of the liquid reaction reagent were dispensed into a 96-well microliter plate made of polystyrene, and measurement was carried out with the Microplate Reader under the conditions described above. As a control, measurement was carried out in the same manner as above except for using a liquid reaction reagent (containing no β-1,3-glucan) prepared by using 175 μl of distilled water in place of the β-1,3-glucan solution.

[Results]

Table 1 shows onset time [a time (sec.) required for OD to reach onset OD=0.01] values obtained by use of the PG standard solutions. Table 2 shows onset time [a time (sec.) required for OD to reach onset OD=0.01] values obtained by use of the β G standard solutions.

TABLE 1

| PG concentration | Onset time (sec.) | | |
|---|---|---|---|
| (ng/ml) | No sugar compound | Schizophyllan | Krestin ™ |
| 0 | nd | nd | nd |
| 1 | 3348 | 3978 | 5292 |
| 10 | 2178 | 2592 | 3420 |
| 100 | 1575 | 1908 | 2412 |
| 1000 | 1359 | 1620 | 1998 |

*The symbol nd in the table indicates that OD did not reach onset OD within the measurement time.

TABLE 2

| β G concentration | Onset time (sec.) | | |
|---|---|---|---|
| (ng/ml) | No sugar compound | Schizophyllan | Krestin ™ |
| 0 | nd | nd | nd |
| 0.01 | 5850 | nd | nd |
| 0.1 | 3762 | nd | nd |
| 1 | 2718 | nd | nd |
| 10 | 1962 | nd | nd |
| 100 | 1476 | 3870 | 5580 |
| 1000 | 1224 | 2916 | 4122 |
| 10000 | 918.0 | 2232 | 2592 |

*The symbol nd in the table indicates that OD did not reach onset OD within the measurement time.

On the basis of the results shown in Table 1, there were obtained calibration curves (on log-log graph paper) showing the relationship between PG concentration and onset time in the case of using each of the liquid reaction reagent containing no β-1,3-glucan, the liquid reaction reagent containing schizophyllan and the liquid reaction reagent containing Krestin™. All the calibration curves obtained were satisfactory. On the basis of the data shown in Table 2, the values obtained for the β G standard solutions by use of each liquid reaction reagent were converted to PG concentrations by using the calibration curve obtained above by use of said liquid reaction reagent. The results obtained are shown in Table 3.

TABLE 3

| β G concentration | PG converted value | | |
|---|---|---|---|
| (ng/ml) | No sugar compound | Schizophyllan | Krestin ™ |
| 0 | — | — | — |
| 0.01 | 0.00900 | — | — |
| 0.1 | 0.248 | — | — |
| 1 | 2.930 | — | — |

TABLE 3-continued

| β G concentration | PG converted value | | |
|---|---|---|---|
| (ng/ml) | No sugar compound | Schizophyllan | Krestin ™ |
| 10 | 34.9 | — | — |
| 100 | 304 | 0.749 | 0.457 |
| 1000 | 1260 | 6.57 | 3.85 |
| 10000 | 11200 | 51.1 | 101 |

As is clear from the results shown in Table 3, when the present sugar compound, i.e., schizophyllan or Krestin™, is incorporated into the reagent, the compound can inhibit the activation of β GRP by β G with almost no influence on the PG measurement. In other words, it can be seen that a reagent specific for PG can easily be obtained by adding the present sugar compound to a body fluid of an insect.

EXAMPLE 2

Study of the reactivity of the body fluid containing the present sugar compound with the PG β G mixed solution

[Reagents]

(1) the reagent; The same as in Experiment Example 1.

(2) DOPA • calcium solution; The same as in Experiment Example 1.

(3) β-1,3-Glucan solutions (schizophyllan, Krestin™); The same as in Example 1.

(4) PG standard solutions; The same as in Example 1.

(5) β G standard solutions; The same as in Example 1.

(6) PG β G mixed solutions; 10 ng/ml of PG standard solution and 10 ng/ml of β G standard solution were mixed at 1:1 (by volume) to prepare 5 ng/ml of PG β G mixed solution. In the same way, 100 ng/ml of PG standard solution and 100 ng/ml of β G standard solution were mixed at 1:1 (by volume) to prepare 50 ng/ml of PG β G mixed solution.

[Measuring instrument]

The same as in Experiment Example 1.

[Procedure]

Onset time of PG β G mixed solution or PG standard solutionn were measured by the same method as Example 1.

[Results]

Table 4 shows onset time [a time (sec.) required for OD to reach onset OD=0.01] values obtained by using the PG β G mixed solutions.

Calibration curves (on log-log graph paper) showing the relationship between PG concentration and onset time in the case of using PG standard solution were obtained by the same method as Example 1.

The onset time values of PG β G mixed solutions were converted to PG concentrations by using the calibration curve obtained above. The results are also shown in Table 4.

TABLE 4

| | Schizophyllan | | Krestin ™ | |
|---|---|---|---|---|
| PG concentration in the PG β G solution (ng/ml) | onset time (sec.) | PG concentration (ng/ml) | onset time (sec.) | PG concentration (ng/ml) |
| 0 | nd | — | nd | — |
| 5 | 5094 | 3.55 | 5355 | 3.96 |
| 50 | 3060 | 58.6 | 3555 | 54.4 |

*The symbol nd in the table 4 indicates that OD did not reach onset OD within the measurement time.

As is clear from the results shown in Table 4, when the present sugar compound, i.e., schizophyllan or Krestin™, is incorporated into the reagent, the compound can inhibit the activation of β GRP by β G with almost no influence on the PG measurement. In other words, it can be seen that a reagent specific for PG can easily be obtained by adding the present sugar compound.

The present invention provides a novel inhibitor of the activation of β GRP in a body fluid of an insect, a process for inhibiting the activation by use of said inhibitor, an agent for treating a body fluid of an insect, a process for the treatment by use of said agent, a reagent for measuring PG simply and effectively, and a process for measuring PG. The present invention is markedly effective in that a reagent for PG measurement, which are obtainable from a body fluid of an insect, can easily be obtained.

What is claimed is:

1. A reagent for measuring peptidoglycan comprising a body fluid of an insect and a polysaccharide having two or more β 1→3 linkages in which 10% or more of sugar residues of the polysaccharide have a substituent at the 6-position.

2. A liquid reagent for measuring peptidoglycan comprising a body fluid of an insect and a polysaccharide having two or more β 1→3 linkages in which 10% or more of sugar residues of the polysaccharide have a substituent at the 6-position, whereby the polysaccharide inhibits a βGlucan recognition protein of the insect body fluid and peptidoglycans can activate the proPO cascade in thus obtained insect body fluid.

3. A two solution reaction process for measuring peptidoglycan, which comprises the steps of:

reacting a sample solution with a reagent solution obtained by dissolving a polysaccharide having two or more β 1→3 linkages in which 10% or more of sugar residues of the polysaccharide have a substituent at the 6-position in a solvent and mixing the reagent solution with the sample solution containing body fluid of an insect to make them present together, measuring a reaction time required for the absorbance of the reaction solution to reach a predetermined threshold value, and calculating the peptidoglycan content of the sample from thus obtained reaction time and a calibration curve showing the relationship between peptidoglycan concentration and reaction times which have previously been obtained by use of standard solutions containing known concentrations of peptidoglycan by the same procedure as the case of sample.

4. A two solution reaction process for inhibiting the activation of βGlucan recognition protein, which comprises dissolving a polysaccharide having two or more β 1→3 linkages in which 10% or more of sugar residues of the polysaccharide have a substituent at the 6-position in a solvent solution and mixing the solvent solution containing the polysaccharide with a sample solution containing a body fluid of an insect, whereby the polysaccharide inhibits the βGlucan recognition protein of the insect body fluid and peptidoglycans can activate the proPO cascade in thus obtained insect body fluid.

5. A process for measuring peptidoglycan, which comprises reacting a sample with a reagent obtained by dissolving a polysaccharide having two or more β 1→3 linkages in which 10% or more of sugar residues of the polysaccharide have a substituent at the 6-position in a body fluid of an insect to make them present together or mixing a solution containing the polysaccharide with the body fluid, measuring a reaction time required for the absorbance of the reaction solution to reach a predetermined threshold value, calculating the peptidoglycan content of the sample from thus obtained reaction time and calibration curve showing the relationship between peptidoglycan concentration and reaction times which have previously been obtained by use of standard solutions containing known concentrations of peptidoglycan by the same procedure as the case of sample.

6. A process for inhibiting the activation of β-glucan recognition protein, which comprises dissolving a polysaccharide having two or more β 1→3 linkages in which 10% or more of sugar residues of the polysaccharide have a substituent at the 6-position in a body fluid of an insect to make them present together or mixing a solution containing a polysaccharide with the body fluid.

7. A process according to claim 6, wherein the insect is Lepidopterg, Diptera, Orthoptera or Coleoptera.

8. A process according to claim 6, wherein the insect is Bombyx.

9. A process according to claim 6, wherein the polysaccharide is a compound having one or more units composed of one sugar residue having a substituent at the 6-position and two sugar residues having no substituent at the 6-position, the sugar residues being bonded together β 1→3 linkages with one another.

10. A process according to claim 9, wherein each of the sugar residues is a hexose residue.

11. A process according to claim 10, wherein the sugar residues are a glucose residue and the substituent at the 6-position is a glucose residue.

12. A process according to claim 6, wherein the polysaccharide is schizophyllan, carboxymethylated curdlan, laminarin, laminaran, or a glycoprotein derived from *Coriolus versicoler*.

13. A process according to claim 6, wherein the polysaccharide is schizophyllan or a glycoprotein derived from *Coriolus versicoler*.

* * * * *

UNITED STATES PATENT AND TRADEMARK OFFICE
CERTIFICATE OF CORRECTION

PATENT NO.    : 6,274,565 B1  
DATED         : August 14, 2001  
INVENTOR(S)   : Yoichi Katsumi It is certified that error appears in the above-identified patent and that said Letters Patent is hereby corrected as shown below:

<u>Column 14,</u>
Line 29, should read as follows:

-- 7. A process according to claim 6, wherein the insect is Lepidoptera, Diptera, Orthoptera or Coleoptera. --

Line 50, add new claim 14, as follows:

-- 14. An agent for treating a body fluid of an insect comprising a polysaccharide having two or more $\beta$ 1-3 linkages in which 10% or more of sugar residues of the polysaccharide have a substituent at the 6 position. --

Signed and Sealed this

Eighteenth Day of June, 2002

*Attest:*

JAMES E. ROGAN  
*Attesting Officer*     *Director of the United States Patent and Trademark Office*